United States Patent [19]

Strohmeyer et al.

[11] 3,957,684

[45] May 18, 1976

[54] CONTINUOUS MANUFACTURE OF SOLUTIONS OF COBALT CARBONYL AND COBALT CARBONYL HYDRIDE IN ORGANIC SOLVENTS

[75] Inventors: Max Strohmeyer, Limburgerhof; Hans Juergen Nienburg, Heidelberg; Rudolf Kummer, Frankenthal; Heinz Hohenschutz, Mannheim, all of Germany

[73] Assignee: BASF Aktiengesellschaft, Ludwigshafen (Rhine), Germany

[22] Filed: June 24, 1974

[21] Appl. No.: 482,251

[30] Foreign Application Priority Data
June 27, 1973 Germany............................ 2332638

[52] U.S. Cl............................... 252/428; 252/443; 423/417; 423/418
[51] Int. Cl.².......................................... B01J 27/20
[58] Field of Search ............ 252/428, 443; 423/417, 423/418

[56] References Cited
UNITED STATES PATENTS
2,691,046  10/1954  Hasek............................ 252/443 X FOREIGN PATENTS OR APPLICATIONS
1,071,683  12/1959  Germany........................... 252/443

*Primary Examiner*—Patrick P. Garvin
*Attorney, Agent, or Firm*—Johnston, Keil, Thompson & Shurtleff

[57] ABSTRACT

Solutions of cobalt carbonyl and cobalt carbonyl hydride in organic solvents are prepared by treating aqueous solutions of cobalt salts with carbon monoxide and hydrogen at a temperature of from 50° to 200°C and a pressure of from 50 to 500 atmospheres in the presence of solvents which are sparingly water-miscible or are water-immiscible and which have a content of cobalt carbonyl, cobalt carbonyl hydride or mixtures thereof, the starting materials and the organic solvents being passed cocurrently through a zone in which a turbulent flow is maintained. The improvement includes using n-butanol as solvent. Solutions of cobalt carbonyl and cobalt carbonyl hydride in n-butanol are suitable as catalyst solutions for oxo syntheses.

7 Claims, No Drawings

CONTINUOUS MANUFACTURE OF SOLUTIONS OF COBALT CARBONYL AND COBALT CARBONYL HYDRIDE IN ORGANIC SOLVENTS

This invention relates to an improved process for the continuous manufacture of solutions of cobalt carbonyl and cobalt carbonyl hydride in organic solvents by treating aqueous solutions of cobalt salts with carbon monoxide and hydrogen at temperatures of from 50° to 200°C and pressures of from 50 to 500 atmospheres in the presence of organic solvents which are sparingly water-miscible or are water-immiscible and which have a content of cobalt carbonyl and cobalt carbonyl hydride, the srarting materials and the organic solvents being passed cocurrently through a zone in which a turbulent flow is maintained.

German Published Application No. 1,071,683 discloses a process in which aqueous solutions of cobalt salts are treated with carbon monoxide and hydrogen in the presence of alkanals or alkanols. This process has the drawback, however, that after a treatment period of, say, 6 hours only part of the cobalt(II) ions present in the aqueous solution have been converted to cobalt carbonyl hydride. Such a process is not suitable for continuous operation on an industrial scale, since it requires too much time and necessitates the use of very expensive and large apparatus. German Published Application No. 1,767,277 discloses that cobalt carbonyl hydride may be obtained by treating aqueous solutions of cobalt acetate with carbon monoxide and hydrogen in the presence of aldehydes which are not completely miscible with water. In this case, there is obtained a solution of cobalt carbonyl hydride in the aldehyde used, the aqueous solution being circulated. This method has not been adopted industrially since it also involves a long reaction time of about 1 hour to produce an adequate concentration of cobalt carbonyl hydride in the aldehyde.

It is an object of the invention to provide a process which requires only short reaction times and thus makes it possible to use less expensive small-size equipment. It is a further object of the invention to provide a process which produces a solution of cobalt carbonyl and cobalt carbonyl hydride in butanol in a single pass, which solution may be directly used as catalyst solution in oxo synthesis reactions.

In accordance with the present invention these and other objects and advantages are achieved in an improved process for the manufacture of solutions of cobalt carbonyl and cobalt carbonyl hydride in organic solvents by treating aqueous solutions of cobalt salts with carbon monoxide and hydrogen at a temperature of from 50° to 200°C and a pressure of from 50 to 500 atmospheres in the presence of organic solvents which are sparingly water-miscible or are water-immiscible and which have a content of cobalt carbonyl and/or cobalt carbonyl hydride, the starting materials and the organic solvent being passed cocurrently through a zone in which a turbulent flow is maintained, the improvement comprising the use of n-butanol as solvent.

Usually, the starting materials are aqueous solutions of cobalt sulfate, chloride or nitrate and also of fatty acid salts of cobalt which are water-soluble. Of particular industrial significance are cobalt salts of fatty acids of from 1 to 4 carbon atoms. Suitable cobalt salts are, for example, cobalt chloride, cobalt nitrate, cobalt formate, cobalt acetate and cobalt butyrate.

Advantageously, aqueous solutions containing from 0.1 to 3% by weight of cobalt in the form of said salts are used. However, solutions of higher concentrations may also be used. Of particular industrial significance are aqueous solutions of cobalt salts such as are obtained in the treatment of oxo reaction mixtures with aqueous acetic acid and gases containing molecular oxygen. Typical solutions contain, for example, from 0.2 to 2.5% of cobalt formate, from 0.3 to 6% cobalt acetate and from 0.4 to 10% of cobalt butyrate, by weight.

Treatment is effected with a mixture of carbon monoxide and hydrogen. This gas mixture advantageously contains carbon monoxide and hydrogen in a ratio of 2:1 to 1:2 by volume. The gas mixture is advantageously used in excess, for example an excess of up to 10 times the stoichiometric amount.

The treatment is carried out at temperatures of from 50° to 200°C. Particularly good results are obtained at temperatures of from 100° to 170°C. Furthermore, a pressure of from 50 to 500 atmospheres is maintained during the reaction and particularly satisfactory results have been obtained using pressures of from 200 to 300 atmospheres.

The essential feature of the invention is that n-butanol is used as the organic solvent. Advantageously, the n-butanol used has a content of cobalt carbonyl and/or cobalt carbonyl hydride, this content advantageously being from 0.05 to 12% and in particular from 0.1 to 1.0% (equivalent to a cobalt content of about 0.02 to 4.0%), by weight. The use of from 0.5 to 5 parts by volume of n-butanol per part by volume of aqueous cobalt salt solution has proved satisfactory.

The starting materials, i.e. the aqueous cobalt salt solution, carbon monoxide and hydrogen, and the n-butanol having a content of cobalt carbonyl and/or cobalt carbonyl hydride are passed cocurrently through a zone in which a turbulent flow is maintained. Advantageously, the reaction is carried out in a turbulence tube, i.e. a zone in which the l/d ratio is from 100 to 10,000:1. The equipment for maintaining a turbulent flow contains a packing, orifice plates or nozzles. The residence time in this zone is preferably from 30 to 120 seconds.

The resulting mixture is then separated into its phases, i.e. a gaseous phase essentially consisting of carbon monoxide and hydrogen and entrained cobalt carbonyl and an aqueous phase containing unreacted cobalt ions and non-extracted cobalt carbonyl hydride and a butanol phase in which the major portion of cobalt carbonyl and cobalt carbonyl hydride is dissolved. From 25 to 80% of the butanol solution obtained is recycled to the reaction in admixture with fresh n-butanol, whilst the remainder is used as a catalyst solution in oxo synthesis reactions. The aqueous phase produced is conveniently used for the removal of cobalt from the crude reaction mixture.

The process of the invention is illustrated in the following Example.

EXAMPLE

A pressure turbulence tube of stainless steel having a length of 110 cm and an internal diameter of 4 mm and surrounded by a heating jacket is completely filled with rings (3 × 3 mm) of V2A steel gauze. The unoccupied volume of the tube is 12 c.c. At one end of the tube there are fed 100 ml/hr of aqueous cobalt acetate solution (1% of $Co^{2+}$), saturated with butanol, together with 100 ml/hr of a solution of cobalt carbonyls in n-butanol (1.5% Co) and together with 80 l/hr (S.T.P.) of an equimolar mixture of carbon monoxide and hydrogen. The liquids are preheated to about 100°C before entering the tube. The tube is heated with steam and the temperature at the end of the tube is 120°C. The pressure in the tube is 280 atmospheres. The average residence time of the mixture in the tube is from 85 to 90 seconds. When the mixture leaves the tube, the gas is separated and then the aqueous and organic phases are separated from each other. The aqueous phase, which contains 0.16% of $Co^{2+}$ and 0.23% of cobalt in the form of cobalt carbonyl hydride, is vented to atmospheric pressure and combined with the aqueous phase coming from the oxidative decobaltation of the oxidation product. 75 ml of the organic phase, which contains from 1.95 to 2.0% of cobalt in the form of cobalt carbonyl and cobalt carbonyl hydride, are recycled to the turbulence tube together with 25 ml of fresh n-butanol, whilst 25 ml of said organic phase are fed with the gas phase to an oxidizing reactor in which propylene is converted to butyraldehydes or butanols.

COMPARATIVE EXAMPLE

Example 1 is repeated except that other water-miscible solvents are used. The concentrations of cobalt carbonyl and cobalt carbonyl hydride obtained are listed below:

| | |
|---|---|
| isobutanol | 1.3% w/w of cobalt |
| isobutyraldehyde | 0.7% w/w of cobalt |
| 2-ethylhexanol | 0.2% w/w of cobalt |
| $C_4$ high boilers (distillation residues from hydroformylation of propylene) | 0.4% w/w of cobalt. |

The resulting solutions of cobalt carbonyls in the appropriate solvents are less suitable or entirely unsuitable for direct use as catalyst solutions in oxo synthesis reactions, on account of their lower content of cobalt.

We claim:

1. In a process for the manufacture of a solution of cobalt carbonyl and cobalt carbonyl hydride in an organic solvent which is water-immiscible or sparingly water-miscible by treating an aqueous solution of a cobalt salt with carbon monoxide and hydrogen at a temperature of from 50° to 200°C and a pressure of from 50 to 500 atmospheres in the presence of said organic solvent, the improvement which comprises using n-butanol as said organic solvent with an initial content of 0.02 to 4% by weight of cobalt dissolved in the form of cobalt carbonyl, cobalt carbonyl hydride or mixtures thereof, the aqueous solution and said n-butanol with said initial content of cobalt being fed cocurrently for treatment with said carbon monoxide and hydrogen through a zone in which a turbulent flow is maintained.

2. A process as claimed in claim 1, wherein aqueous solutions of cobalt salts with fatty acids of from 1 to 4 carbon atoms are used.

3. A process as claimed in claim 1, wherein aqueous solutions are used which contain from 0.1 to 3% by weight of cobalt salts, calculated as cobalt metal.

4. A process as claimed in claim 1, wherein from 0.5 to 5 parts by volume of n-butanol are used per part by volume of aqueous cobalt salt solution.

5. A process as claimed in claim 1, wherein said n-butanol has an initial content of about 0.02 to 1.5% by weight of cobalt.

6. A process as claimed in claim 5, wherein the aqueous solution contains from 0.1 to 3% by weight of cobalt salt, calculated as cobalt metal.

7. A process as claimed in claim 6, wherein from 0.5 to 5 parts by volume of n-butanol are used per part by volume of aqueous cobalt salt solution.

* * * * *